United States Patent [19]

Possis et al.

[11] Patent Number: 4,610,661
[45] Date of Patent: Sep. 9, 1986

[54] PERFUSION DEVICE

[75] Inventors: Zinon C. Possis; Demetre M. Nicoloff, both of Edina, Minn.

[73] Assignee: Possis Medical, Incorporated, Minneapolis, Minn.

[21] Appl. No.: 620,380

[22] Filed: Jun. 13, 1984

[51] Int. Cl.$^4$ .................................. A61M 31/00
[52] U.S. Cl. ...................... 604/52; 604/113; 604/264
[58] Field of Search .................. 604/53-54, 604/93, 113, 280, 52, 73-74, 115, 174, 176, 264, 275; 128/399-400

[56] References Cited

U.S. PATENT DOCUMENTS

| 330,084 | 11/1885 | Allen | 604/275 |
|---|---|---|---|
| 603,815 | 5/1898 | Duke . | |
| 686,985 | 11/1901 | Miller . | |
| 753,990 | 3/1904 | Lutje . | |
| 889,810 | 6/1908 | Robinson . | |
| 1,226,473 | 5/1917 | Daniel . | |
| 1,732,566 | 10/1929 | McKendrick . | |
| 3,066,672 | 12/1962 | Crosby, Jr. et al. . | |
| 3,474,786 | 10/1969 | Spademan . | |
| 3,605,752 | 9/1971 | Schlesinger . | |
| 3,610,240 | 10/1971 | Harautunein . | |
| 3,670,727 | 6/1972 | Reiterman . | |
| 3,690,323 | 9/1972 | Wortman et al. . | |
| 3,709,223 | 1/1973 | Macalalad et al. . | |
| 3,784,063 | 1/1974 | Otis et al. | 604/73 |
| 3,817,251 | 6/1974 | Hasson . | |
| 4,182,329 | 1/1980 | Smit et al. . | |
| 4,232,669 | 11/1980 | Nitshke . | |
| 4,416,280 | 11/1983 | Carpenter et al. | 128/399 |
| 4,509,532 | 4/1985 | DeVries . | |

OTHER PUBLICATIONS

Cannula for Dispensing Cardioplegic Liquid (Prior Art).
Technical Bulletin #1, Texas Medical Products, Inc.
Cardiovascular Diseases, Bulletin of Texas Heart Instit. vol. 6.
Aortic Root Cannula DLP, Inc. 10/1979.
Aortic Root Cannula with Attached Vent Line DLP, Inc. 2/1981.
William Harvey® Extracorporeal Cannulae, Bard, Inc.
USCI Catologue 1974/5070107.

Primary Examiner—C. Fred Rosenbaum
Assistant Examiner—Michelle N. Lester
Attorney, Agent, or Firm—Burd, Bartz & Gutenkauf

[57] ABSTRACT

A device used to introduce a cardioplegic solution into a coronary artery has an elongated tube and a pliable annular member mounted on the outlet end of the tube. The annular member is a cup-shaped pliable plastic member having an open end that is larger than the inlet arterial opening to the coronary artery. The open end of the cup-shaped member fits over inlet opening to direct the cardioplegic solution into the coronary artery.

27 Claims, 11 Drawing Figures

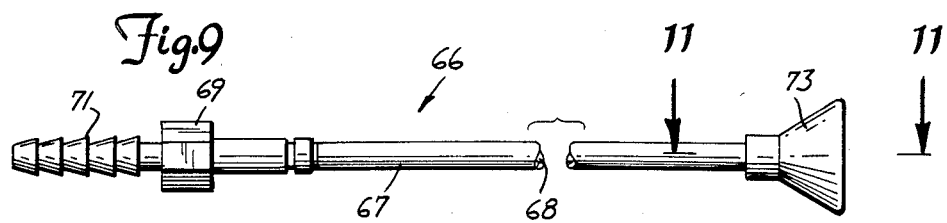
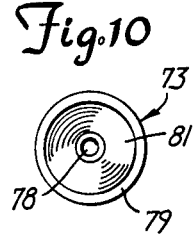
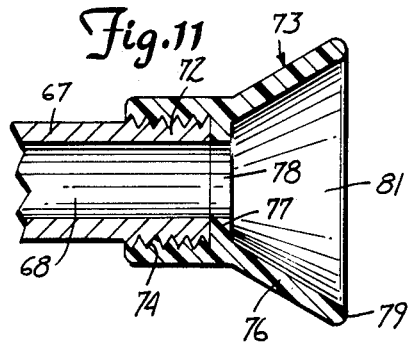

ic fluid from a supply of the fluid to the inlet opening of a coronary artery. An annular means having a chamber open to the passage is attached to to the outlet end of the tubular member for directing the cardioplegic fluid into the inlet opening of the coronary artery. The annular means has a pliable annular sleeve surrounding the chamber. The sleeve has an annular continuous outer edge adapted to be located in sealing engagement with aorta tissue surrounding the inlet opening of the coronary artery. The cardioplegic fluid is delivered under pressure to the chamber of the annular sleeve. The sleeve serves as a conduit that guides the cardioplegic fluid into the coronary artery without inserting any portion of the device into the coronary artery. The pliable sleeve does not traumatize the tissue around the coronary ostia and sensitive lumen of the coronary arteries. The annular sleeve is a pliable plastic cup-shaped member having a continuous circular outer edge. The outer edge engages the aorta tissue that surrounds the inlet opening into the coronary artery forming a seal therewith that minimizes the escape of cardioplegic fluid into the aorta and prevents the entrance of air into the coronary arteries.

The device for introducing cardioplegic fluid into a coronary artery is versatile in use as different sizes and shapes of the device are not needed to perfuse the coronary arteries of patients. Cardioplegic solution can be administered to the left and right arteries with the same device. The device is useable with infants and children without risk of damage to the coronary ostia or to the coronary arteries. The device is effective in use as it avoids the inadvertant perfusion of only one branch of a coronary artery. Perfusion of the coronary arteries with a cardioplegic fluid can be accomplished with a minimum of time during the surgical procedure.

PERFUSION DEVICE

TECHNICAL FIELD

The field of invention is medical instruments for carrying fluid to a body and directing the fluid into a selected body cavity, such as the lumen of a coronary artery.

BACKGROUND OF INVENTION

In aortic valve replacement surgery, a cardioplegic solution or fluid is introduced into the coronary arteries to lower the temperature of the heart and make it motionless. A single cannula is used to dispense the cardioplegic solution into each coronary artery. The cannula is an elongated flexible tube having an enlarged head at its distal end. An example of a cannula for dispensing cardioplegic solution into the heart as shown by Carpenter et al in U.S. Pat. No. 4,416,280. A cannula of a selected size is slipped into the coronary lumen until the entire head engages the wall of the coronary artery. Forcing the cannula into passage of the coronary artery can traumatize the artery tissue and cause scarring. The left coronary artery in some patients bifurcates a few millimeters from the wall of the aorta. This makes the cannula insertion difficult as there is insufficient length of the coronary artery to accommodate the entire head of the cannula.

The right coronary artery in some patients makes a right angle turn in close proximity from its origin from the aorta. The insertion of a cannula to the right coronary artery can injure the artery at the point of the angulation or bend in the artery. The cannula must be gently inserted to safely make a right angle turn. The use of the cannula to achieve cardioplegia utilizes valuable surgeon's time during the operating procedure. The cannula can cause trauma to the coronary ostia and to the proximal portion of the coronary artery.

In certain operative procedures in infants and children with associated aortic insufficiency, it is not possible to utilize cardioplegic solution, because coronary perfusion cannulas of sufficient small size are not available. Other means are required to lower the temperature of the heart.

SUMMARY OF INVENTION

The invention resides in a device and method used to administer cardioplegic fluid into a coronary artery of a heart through the inlet opening in the aorta. The device has tubular means with a passage for carrying the cardioplegic fluid.

Annular means mounted on one end of the tubular means is retained in engagement with the aorta to control movement of fluid into the coromary artery. The annular means includes a pliable annular member having a passage open to the aorta to allow fluid to flow through the device. The annular member conforms to the contour of the aorta and functions as a guide and seal to confine the fluid to the inlet opening of the coronary artery. The annular member is disclosed as a cup-shaped pliable plastic member and as a pliable ring attached to the fluid discharge end of a tube.

The medical device and method of the invention is useable to introduce a cardioplegic fluid into a coronary artery through an inlet aterial opening or coronary ostia of the coronary artery. The device has an elongated tubular member having an inlet end and an outlet end open to a continuous passage for carrying the cardiople-

DESCRIPTION OF DRAWING

FIG. 9 is a foreshortened side view of a first modification of the medical device of the invention;

FIG. 10 is an end view of the discharge end of the device of FIG. 9; and

FIG. 11 is an enlarged sectional view taken along the line 11—11 of FIG. 9;

DESCRIPTION OF PREFERRED EMBODIMENTS

Figure 1:
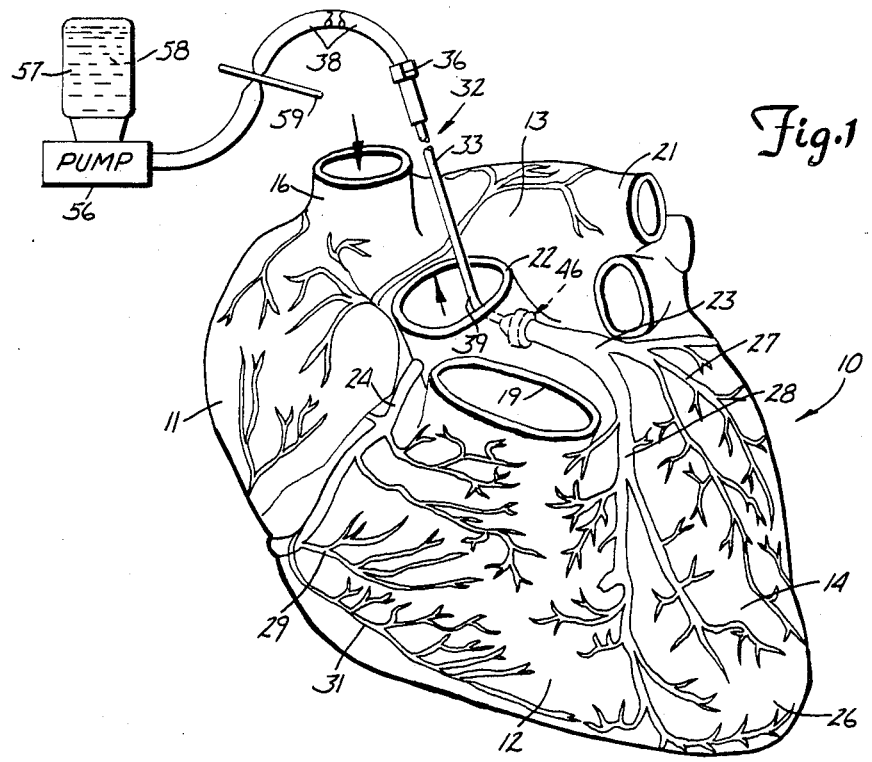
FIG. 1 is a diagrammatic view of a human heart showing the medical device of the invention for introducing a cardioplegic fluid into a coronary artery.

Referring to FIG. 1, there is shown an anterior view of a human heart indicated generally at 10. Heart 10 has a right atrium 11, right ventricle 12, left atrium 13, and left ventricle 14. Blood flows through vena cava 16 into right atrium 11. A heart valve (not shown) controls the flow of blood from right atrium 11 into right ventricle 12. The blood is pumped from the right ventricle 12 through a pulmonary artery 19, which is connected to the lungs. The blood returns from the lungs via pulmonary vein 21 to the left atrium 13. The blood flows from left atrium 13 into left ventricle 14 and is pumped from left ventricle 14 into an aorta 22.

The muscle tissue of the heart is provided with a supply of blood from two coronary arteries 23 and 24. In cardiovascular surgery, the coronary arteries are used to carry cardioplegic solution to the heart tissue to lower the temperature of the heart thereby making it motionless. Left coronary artery 23 extends from aorta 22 along the left side of the heart toward apex 26. Coronary artery 23 has a short common stem leading from an aorta 22 which bifurcates or trifurcates into branches 27 and 28. The length of this stem varies between patients. In some patients the common stem of coronary artery 23 is short and makes a right angle turn. This makes it difficult to insert the entire head of a cannula into the lumen of the artery. Cardioplegic solution forced through the cannula can flow back into the aorta away from the heart. The cannula can injure the artery at the bend in the artery. One of the branches 28 extends toward the anterior interventricular groove and rounds the acute margin of the heart just to the right of apex 26 and ascends a short distance up the posterior interventricular groove to supply blood to the muscle tissue of the heart. Right coronary artery 24 extends down the right side of the heart toward apex 26. Artery 24 has a number of branches 29 and 31 which feed blood to the heart tissue. Right coronary artery 24 arises from the anterior sinus of aorta 22 and runs along the right atrioventricuss sulcus toward apex 26.

Open heart surgery procedures have been developed to replace diseased and damaged natural heart valves with heart valve prosthesis. An example of a heart valve prosthesis is disclosed by Possis in U.S. Pat. No. Re. 31,040. The patient's chest cavity is initially open to expose the heart. Blood by-pass pumps and heart oxygenators are connected to the patient to continue the circulation of blood in the patient's body. A perfusion device 32 is used to introduce a cardioplegic solution into the coronary arteries to lower the temperature of the heart and thereby stop its operation. The heart is motionless during the natural valve excision and the replacement of a prosthetic heart valve.

As shown in FIG. 1, a cardioplegic solution is introduced into coronary artery 23 with a perfusion device or instrument of the invention indicated generally at 32. Device 32 has a rigid elongated tube 33 having a continuous passage 34. Tube 33 is made of malleable material so that it can be bent to fit the anatomical situation. The proximal end of tube 33 is joined to a connector 36 having a nipple 37. The tube 33, connector 36, and nipple 37 is a one-piece tubular member made of stainless steel or plastic. An elongated flexible hose 38 is connected to nipple 37 to transport a cardioplegic solution from a source of the solution to tube 33. An example of a cardioplegic delivery system is disclosed by Carpenter in U.S. Pat. No. 4,416,280.

Figure 2:
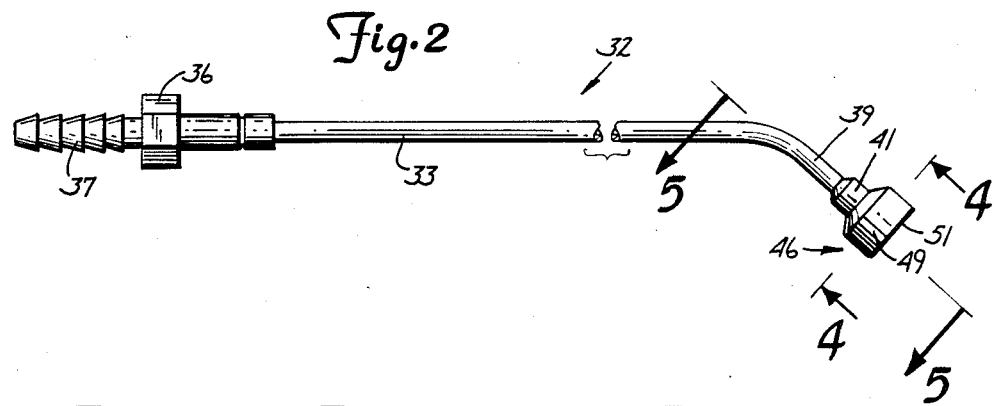
FIG. 2 is a foreshortened side view of the medical device of the invention.
Figure 3:
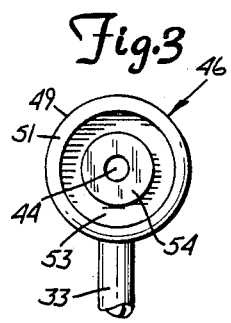
FIG. 3 is an enlarged end view of the discharge end of the medical device of FIG. 2.
Figure 4:
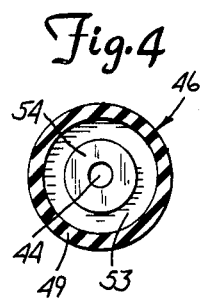
FIG. 4 is an enlarged sectional view taken along the line 4—4 of FIG. 2.

As shown in FIG. 2, tube 33 has a main elongated linear body joined to a distal end 39 terminating in a cylindrical head 41. End 39 projects at an angle of about 45 degrees relative to the longitudinal axis of tube 33. The angular relationship of end 39 relative to the main body of tube 33 can vary.

Figure 5:
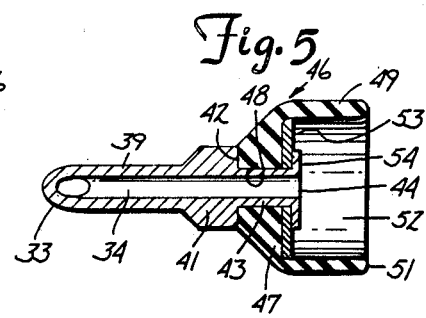
FIG. 5 is an enlarged sectional view taken along the line 5—5 of FIG. 2.

Referring to FIG. 5, head 41 has an annular flat face 42 and an axial tubular projection 43. Projection 43 has an open end 44 in communication with passage 34. An annular member indicated generally at 46 is mounted on head 41. Member 46 is a cup-shaped flexible member having a base 47 located in surface engagement with annular face 42 and a central hole 48. Projection 43 extends through hole 48. A cylindrical flange 49 is joined to the outer peripheral edge of base 47. Flange 49 terminates in a distal rounded circular end 51. Circular end 51 has a continuous and uninterrupted end surface. Flange 49 is a thin cylindrical sleeve that is flexible to minimize injury to the heart tissue. Member 46 surrounds a chamber or pocket 52 for receiving cardioplegic solution from open end 44 of projection 43.

A flat annular ring or washer 53 engages the inside of base 47. Ring 53 fits over projection 43 and is retained thereon with an outwardly directed annular lip or flange 54. Lip 54 is the turned end of projection 43 that holds member 46 and ring 53 on head 41. Member 46 is made of a pliable and flexible material, such as rubber or plastic. The material has memory as it returns to its original shape as soon as the deformation force has been removed. As an example, the material of member 46 can be a flexible and pliable polyethylene plastic having 30 to 40 durometer. The entire annular member 46 can be made from a medical grade silicone elastomer. Other materials can be used to form member 46.

Returning to FIG. 1, hose 38 is connected to a pump 56 supporting a container 57. The cardioplegic solution or medication 58 in container 57 is pumped with pump 56 into hose 38 under a pressure of approximately 100 mm Hg. A scissors-type clamp 59 associated with hose 38 is used to control the flow of cardioplegic solution through tube 33 and into coronary artery 23.

Figure 6:
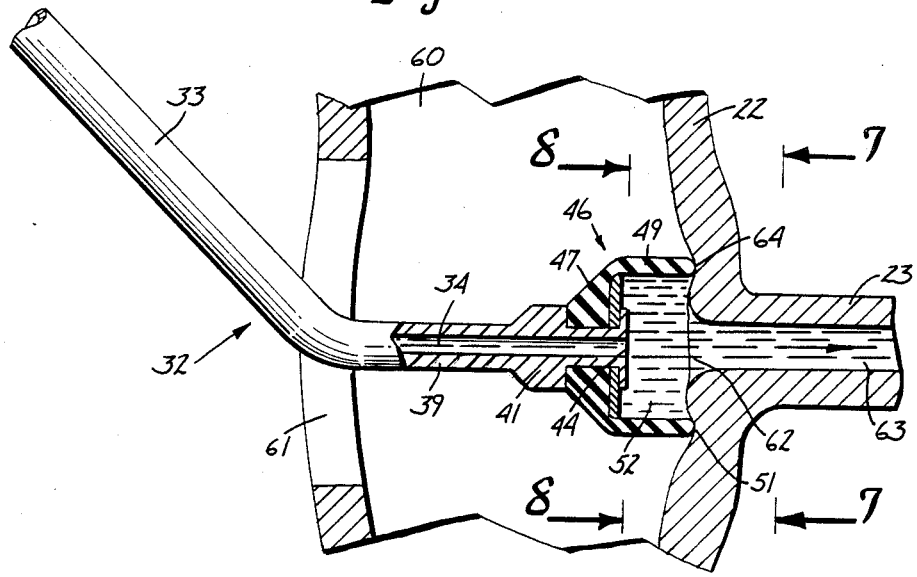
FIG. 6 is an enlarged sectional view of the aorta and coronary artery extending therefrom showing the medical device, partly sectioned, introducing cardioplegic fluid into the coronary artery.
Figure 7:
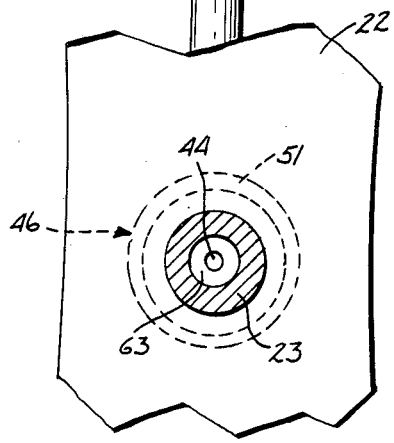
FIG. 7 is a sectional view taken along the line 7—7 of FIG. 6.
Figure 8:
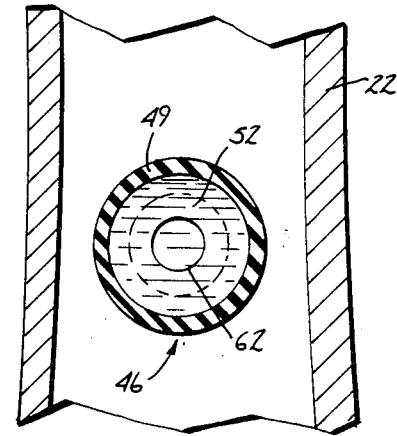
FIG. 8 is a sectional view taken along the line 8—8 of FIG. 6.

Referring to FIGS. 6 to 8, in use, an incision 61 is made in the wall of aorta 22 generally opposite the inlet opening 62 to coronary artery 23 to provide access to the aorta passage 60 adjacent the entrances to the coronary arteries 23 and 24. The surgeon introduces the distal end 39 of instrument 32 into the coronary artery passage 60 and locates member 46 in alignment with the ostia or inlet opening 62 of coronary artery 23. This permits the flow of cardioplegic solution into the lumen 63 of coronary artery 23. The surgeon, with a light finger pressure, holds member 46 in engagement with an annular portion 64 of the aorta surrounding ostia 62. This aligns chamber 52 with ostia 62, as shown in FIG. 6. The aorta tissue 64 is slightly compressed to insure a seal between the distal circular end 51 of flange 49 and the aorta tissue around opening 62. Chamber 52 is larger than ostia 62 to prevent closing of the ostia due to the pressure of flange 49 on the aorta and to allow for any misalignment of member 46 relative to ostia 62.

The pump 56 is operated to place the cardioplegic solution under pressure. The clamp 59 is released to allow the solution to flow through hose 38 and into tube 33. The solution is discharged through the open end 44 into the chamber 52. Flange 59, being located in sealing engagement with the inside wall of aorta 22, insures that the cardioplegic solution is directed into ostia 62 and lumen 63 of coronary artery 23. The right coronary artery 24 is perfused with cardioplegic solution in the same manner.

Referring to FIGS. 9–11, there is shown a coronary perfusion device of this invention indicated generally at 66. Device 66 has an elongated linear tube 67 having a continuous passage 68. Tube 67 is an elongated rigid material, such as stainless steel or plastic. A connector 69 is located on the proximal end of tube 67. Connector 69 has a nipple 71 for accommodating hose 38 for delivering cardioplegic solution to tube 67.

An annular member indicated generally at 73 is mounted on the proximal end of tube 67. Member 73 has a cylindrical base 74 threaded on the distal end of tube 67. An annular cone-shaped flange 76 extends outwardly from base 74. Flange 76 terminates in a circular rounded end 79. Base 74 has an inwardly directed annular rib 77 that engages distal end 72 of tube 67 to lock member 73 on tube 67. Rib 77 surrounds an outlet or open end 78 for directing the cardioplegic solution into a chamber 81 surrounded by flange 76.

Member 73 is a one-piece cup-shaped member made of plastic or metal. Base 74 and flange 76 can be rigid material, such as stainless steel or rigid plastic. Flange 76 can be made of flexible material, such as the material of member 46. The member 73 can be removed from tube 67 so that the tube can be subsequently used with a new member.

The coronary perfusion devices 32 and 66 are useable with the wide range of coronary artery diameters, which range from approximately 4 mm. to 9 mm. The coronary perfusion devices of this invention enable the surgeon to save a considerable amount of time, in that the pre-selection of the exact sizes of formerly used cannula is no longer necessary. A single coronary perfusion device is useable with all sizes of coronary artery diameters.

While there has been shown and described the preferred embodiments of the coronary perfusion device of the invention, it is understood that changes in the shape, size, materials, structure and use of the device may be made by those skilled in the art without departing from the invention. The invention is defined in the following claims.

The embodiments of the invention in which an exclusive property or privilege is claimed are defined as follows:

1. An apparatus for transporting a cardioplegic fluid from a supply of cardioplegic fluid to a coronary artery having a blood inlet opening in the aorta to perfuse the coronary artery with cardioplegic fluid, said apparatus comprising: a supply of cardioplegic fluid, an elongated tubular member having an inlet end and an outlet end, hose means connecting said inlet end to said supply of cardioplegic fluid, and annular means attached to the outlet end of the tubular member for accommodating cardioplegic fluid, said annular means including a pliable annular sleeve which forms a chamber about said outlet end, said sleeve having a continuous annular outer end larger than the size of the blood inlet opening in the aorta whereby said chamber has a transverse size greater than said blood inlet opening, said annular outer end being adapted to be held in engagement with an annular portion of the aortic tissue surrounding the blood inlet opening of the coronary artery whereby cardioplegic fluid may flow from the container through the hose, the tubular member, the chamber and through said inlet opening into the coronary artery.

2. The apparatus of claim 1 wherein: the tubular member is an elongated bendable tube.

3. The apparatus of claim 2 wherein: the tube has a body section and an end section extended at an angle relative to the body section.

4. The apparatus of claim 3 wherein: the angle is an obtuse angle relative to the body section.

5. The apparatus of claim 1 wherein: the annular means is a pliable cup-shaped member having a base with a hole, said outlet end of the tubular member being disposed in said hole and attached to said base, said annular sleeve being joined to said base.

6. The apparatus of claim 5 wherein: the sleeve is a cylindrical member having an uninterrupted circular outer end.

7. The device of claim 6 wherein: the sleeve is a pliable plastic member.

8. The apparatus of claim 1 wherein: said annular means has a base with a hole, said outlet end of the tubular member being disposed in said hole, and said sleeve includes a pliable cone-shaped member joined to said base, said annular outer end being part of said cone-shaped member.

9. An apparatus for transporting a cardioplegic fluid from a supply of cardioplegic fluid to a coronary artery having a blood inlet opening in the aorta to perfuse the coronary artery with cardioplegic fluid, said apparatus comprising: a supply of cardioplegic fluid, tubular means having a passage for carrying cardioplegic fluid, said tubular means having an inlet end connected to said supply of cardioplegic fluid and an outlet end with annular means connected thereto for directing cardioplegic fluid to the coronary artery, said annular means including a pliable annular member having an annular outer end larger than the blood inlet opening in the aorta, said annular outer end being adapted to be held in engagement with an annular portion of the aortic tissue surrounding the blood inlet opening of the coronary artery whereby cardioplegic fluid may flow from said passage through said inlet opening and into the coronary artery.

10. The apparatus of claim 9 wherein: the annular member is a pliable cup-shaped member and includes means for connecting the cup-shaped member to said outlet end of the tubular means.

11. The apparatus of claim 9 wherein: the tubular means comprises a tube having a body section and an end section extended at an angle relative to the body section.

12. The apparatus of claim 11 wherein: said angle is an obtuse angle.

13. The apparatus of claim 9 wherein: said annular member is a cylindrical sleeve having an uninterrupted circular outer end.

14. The apparatus of claim 9 wherein: said annular member includes a pliable cone-shaped member, said cone-shaped member having an uninterrupted outer end.

15. The apparatus of claim 9 wherein: said tubular means includes a head element attached to the outlet end thereof, said annular means includes an annular cup-shaped member mounted on the head element, said cup-shaped member including said pliable annular member, said pliable annular member comprising: a cylindrical pliable sleeve forming a chamber about the outlet end of the tubular means, said sleeve having an uninterrupted outer end.

16. The device of claim 15 wherein: said tube has a body section and an end section extended at an angle relative to the body section.

17. The device of claim 15 wherein: said sleeve is a pliable plastic member.

18. The device of claim 15 wherein: said sleeve includes a pliable cone-shaped member, said uninterrupted outer end being part of said cone-shaped member.

19. An apparatus for transporting a cardioplegic fluid from a supply of cardioplegic fluid to a coronary artery having a blood inlet opening in the aorta to perfuse the coronary artery with cardioplegic fluid, said apparatus comprising: an elongated tube having passage for carrying cardioplegic fluid, said tube having an inlet end adapted to be connected to a supply of cardioplegic fluid and an outlet end with a pliable annular member mounted thereon, said member having a passage for carrying cardioplegic fluid from said tube and a continuous generally circular outer end having a diameter larger than the transverse size of the blood inlet opening of the coronary artery whereby when said generally circular outer end may be held in engagement with an annular portion of the aortic tissue surrounding the blood inlet opening of the coronary artery so that cardioplegic fluid may flow from said annular member through said inlet opening and into the coronary artery.

20. The apparatus of claim 19 wherein: the annular member has a base with a hole, said outlet end of the tube being disposed in said hole and attached to the base, said annular member having an annular body joined to the base, said generally circular outer end being part of said body.

21. The apparatus of claim 20 wherein: said body is a pliable sleeve joined to the base, said sleeve providing said generally circular outer end and forming a chamber for accommodating cardioplegic fluid.

22. The apparatus of claim 19 wherein: said tube is malleable and is adapted to be shaped to a selected angle.

23. A method for transporting a cardioplegic fluid from a supply of cardioplegic fluid to a coronary artery having a blood inlet opening in the aorta with an elongated tube having a passage for carrying cardioplegic fluid, said tube having an inlet end connected to a supply of cardioplegic fluid, and an outlet end with an annular pliable member mounted thereon, said annular member having a passage for carrying cardioplegic fluid from said tube and a continuous outer end having a transverse size larger than the size of the blood inlet opening of the coronary artery, said method comprising: surgically exposing the heart and opening the wall of the aorta to provide access to the aortic passage, introducing the outlet end of the tube and annular pliable member mounted thereon into the aorta passage, locating the annular pliable member in alignment with the blood inlet opening of the coronary artery with the annular outer end surrounding the blood inlet opening, holding the annular outer end in engagement with an annular portion of aortic tissue surrounding the blood inlet opening, and allowing cardioplegic to flow through said tube and into the coronary artery through said blood inlet opening.

24. The method of claim 23 including: opening the wall of the aorta generally opposite the inlet opening of the coronary artery.

25. The method of claim 23 wherein: the annular pliable member is held in engagement with the aortic tissue with light pressure so that the annular portion of the aortic tissue is compressed against the annular outer end of the annular pliable member.

26. The method of claim 23 wherein: the annular outer end of the annular pliable member is held in sealing relation with said annular portion of the aortic tissue.

27. The method of claim 23 wherein: cardioplegic fluid is pumped into the passage of the tube.

* * * * *